United States Patent
Nieuwenhuis et al.

(10) Patent No.: US 8,970,215 B2
(45) Date of Patent: Mar. 3, 2015

(54) SENSOR DEVICE FOR AND A METHOD OF SENSING PARTICLES

(75) Inventors: Jeroen Hans Nieuwenhuis, Waalre (NL); Godefridus Johannes Verhoeckx, Eindhoven (NL); Menno Willem Jose Prins, Rosmalen (NL); Petrus Johannes Wilhelmus Van Lankvelt, Boekel (NL); Kim Van Ommering, Eindhoven (NL)

(73) Assignee: Koninklijkle Philips N.V., Eindhoven (NL)

( * ) Notice: Subject to any disclaimer, the term of this patent is extended or adjusted under 35 U.S.C. 154(b) by 756 days.

(21) Appl. No.: 12/521,905

(22) PCT Filed: Jul. 26, 2007

(86) PCT No.: PCT/IB2007/052967
§ 371 (c)(1),
(2), (4) Date: Jan. 8, 2010

(87) PCT Pub. No.: WO2008/084343
PCT Pub. Date: Jul. 17, 2008

(65) Prior Publication Data
US 2010/0109653 A1 May 6, 2010

(30) Foreign Application Priority Data

Jan. 12, 2007 (EP) .................................. 07100466

(51) Int. Cl.
*G01N 33/558* (2006.01)
*G01R 33/12* (2006.01)
(Continued)

(52) U.S. Cl.
CPC ................ *G01R 33/12* (2013.01); *B82Y 25/00* (2013.01); *G01R 33/093* (2013.01); *G01R 33/1284* (2013.01); *G01N 15/0656* (2013.01); *G01N 2011/008* (2013.01); *G01N 2015/0053* (2013.01)

USPC .................... 324/303; 435/287.2; 436/518

(58) Field of Classification Search
CPC ................ G01N 33/558; B01L 3/5027; B01L 2300/0816
USPC ................. 184/6.21, 6.22; 137/92; 73/54.01–54.43; 324/204, 306, 353, 324/325, 750.08, 754.15, 92
See application file for complete search history.

(56) References Cited

U.S. PATENT DOCUMENTS 3,861,197 A * 1/1975 Adler .......................... 73/54.31
5,072,610 A 12/1991 Martinoli et al.
(Continued)

FOREIGN PATENT DOCUMENTS

EP 1102054 A2 5/2001
JP 06-316445 * 12/1994 ............. G01N 11/10
(Continued)

OTHER PUBLICATIONS

Mao et al: "Towards Ferrofluidics for u-TAS and Lab On-A-Chip Applications"; Nanotechnology 17, 2006, pp. S34-S47, Institue of Physics Publishing.
(Continued)

*Primary Examiner* — Tung X Nguyen
*Assistant Examiner* — Alesa Allgood

(57) ABSTRACT

A sensor device for sensing particles of a sample, the sensor device including a sensing unit adapted for sensing a detection signal indicative of the presence of the particles, a viscosity measurement unit adapted for measuring the viscosity of the sample, and a correction unit adapted for correcting the detection signal based on the measured viscosity.

18 Claims, 10 Drawing Sheets

(51) Int. Cl.
*B82Y 25/00* (2011.01)
*G01R 33/09* (2006.01)
*G01N 15/06* (2006.01)
*G01N 11/00* (2006.01)
*G01N 15/00* (2006.01)

(56) References Cited

U.S. PATENT DOCUMENTS

| | | | |
|---|---|---|---|
| 6,194,222 B1 * | 2/2001 | Buechler et al. | 436/518 |
| 6,525,334 B1 * | 2/2003 | Brackett | 250/573 |
| 6,727,696 B2 * | 4/2004 | Kruspe et al. | 324/303 |
| 6,751,004 B2 * | 6/2004 | Lassar | 359/280 |
| 7,072,775 B2 * | 7/2006 | Hemp et al. | 702/45 |
| 7,497,997 B2 * | 3/2009 | Glezer et al. | 422/504 |
| 2005/0155415 A1 | 7/2005 | Kurowski et al. | |
| 2006/0010963 A1 * | 1/2006 | Bach et al. | 73/54.01 |
| 2007/0131024 A1 * | 6/2007 | Drahm et al. | 73/54.27 |

FOREIGN PATENT DOCUMENTS

| | | | | |
|---|---|---|---|---|
| JP | 08-178823 | * | 7/1996 | G01N 11/10 |
| JP | 08178823 A | | 7/1996 | |
| WO | 2005010542 A2 | | 2/2005 | |
| WO | 2005010543 A1 | | 2/2005 | |
| WO | 2005090944 A1 | | 9/2005 | |

OTHER PUBLICATIONS

Valberg et al: "Magnetic Particle Motions Within Living Cells:Physical Theory and Techniques"; Biophysical Journal, vol. 52, Oct. 1987, pp. 537-550.

* cited by examiner

SENSOR DEVICE FOR AND A METHOD OF SENSING PARTICLES

FIELD OF THE INVENTION

The invention relates to a sensor device.

The invention further relates to a method of sensing particles.

Moreover, the invention relates to a program element.

Further, the invention relates to a computer-readable medium.

BACKGROUND OF THE INVENTION

A biosensor may be a device for the detection of an analyte that combines a biological component with a physicochemical or physical detector component.

Magnetic biosensors may use the Giant Magnetoresistance Effect (GMR) for detecting biological molecules being magnetic/magnetisable or being labeled with magnetic/magnetisable beads.

In the following, biosensors will be explained which may use the Giant Magnetoresistance Effect.

WO 2005/010542 discloses the detection or determination of the presence of magnetic particles using an integrated or on-chip magnetic sensor element. The device may be used for the magnetic detection of the amount of binding of biological molecules on a micro-array or biochip. Particularly, WO 2005/010542 discloses a magnetic sensor device for determining the presence of at least one magnetic particle and comprises a magnetic sensor element on a substrate, a magnetic field generator for generating an AC magnetic field, a sensor circuit comprising the magnetic sensor element for sensing a magnetic property of the at least one magnetic particle which magnetic property is related to the AC magnetic field, wherein the magnetic field generator is integrated on the substrate and is arranged to operate at a frequency of 100 Hz or above.

JP 8178823 discloses a system for measuring viscosity of viscous material. Shortening the measuring time while sustaining accuracy shall be obtained by employing fine particles of a soft magnetic material as a measuring means and moving the fine particles forcibly at a high speed by applying a magnetic field externally thereto. Fine particles of a soft magnetic material may be produced by quenching the molten soft magnetic material. The fine particles may have a spherical shape and the particle size may be arranged by means of a sieve or a gas flow classifier in order to make the resistance of a viscous material uniform during movement of the fine magnetic particles. When the viscosity is measured, the magnetic fine particles are arranged in a measuring vessel filled with a viscous sample material to be measured and a magnetic field is applied to the vessel from the outside thus moving the magnetic fine particles forcibly at a high speed. The moving speed or moving time is then detected in order to measure the viscosity and the moving speed or moving time itself is an indicator for/measure of viscosity.

However, sufficient accuracy of measurement results may still be problematic under certain circumstances.

OBJECT AND SUMMARY OF THE INVENTION

It is an object of the invention to provide a sensor with a sufficiently fine resolution.

In order to achieve the object defined above, a sensor device for sensing particles, a method of sensing particles, a program element, and a computer-readable medium according to the independent claims are provided.

According to an exemplary embodiment of the invention, a sensor device for sensing particles of a sample is provided, the sensor device comprising a sensing unit adapted for sensing a detection signal indicative of the presence of the particles, a viscosity measurement unit adapted for measuring the viscosity of the sample, and a correction unit adapted for correcting the detection signal based on the measured viscosity.

According to another exemplary embodiment of the invention, a method of sensing particles of a sample is provided, the method comprising sensing a detection signal indicative of the presence of the particles, measuring the viscosity of the sample, and correcting the detection signal based on the measured viscosity.

According to still another exemplary embodiment of the invention, a program element is provided, which, when being executed by a processor, is adapted to control or carry out a method of sensing particles having the above mentioned features.

According to yet another exemplary embodiment of the invention, a computer-readable medium is provided, in which a computer program is stored which, when being executed by a processor, is adapted to control or carry out a method of sensing particles having the above mentioned features.

The electronic sensing scheme according to embodiments of the invention can be realized by a computer program, that is by software, or by using one or more special electronic optimization circuits, that is in hardware, or in hybrid form, that is by means of software components and hardware components.

The term "viscosity" may denote a physical property of a fluidic medium indicative of an interior friction of the fluidic medium and may be a parameter which is proportional, in a laminar approximation, to a ratio between a force applied to particles moving through the medium and a velocity of the particles in the medium.

The term "magnetic particles" may denote any molecules having a magnetic portion, that is to say a paramagnetic, a ferromagnetic, or a ferrimagnetic portion. Such a magnetic portion may be inherent to a specific molecule or may be attached as a separate label or bead to a molecule, for instance to a biomolecule. The term magnetic particles may refer to actual magnetic particles or to magnetisable particles (which are magnetised under the influence of an externally applied magnetic field). When magnetic particles are mentioned this can mean magnetic or magnetisable particles (magnetisable particles require an inhomogeneous field to move them).

According to an exemplary embodiment of the invention, a sensor apparatus may be provided in which the presence of particles in a sample may be detected qualitatively or quantitatively based on measuring a detection signal, more particularly a change of the detection signal with time, wherein a disturbing influence of viscosity modifications in the sample may be suppressed or even eliminated by correcting the detection signal on the basis of a (for instance pre-known) correlation between viscosity and change of the signal. In other words, the (change in the) sensor signal may be not only proportional to the concentration of the particles but may also depend on parameters such as transport rates within the sample which, in turn, may depend on the viscosity of the sample. When a pre-known correlation between a change of the sensor signal and the viscosity of the sample is taken into account and when the viscosity value is measured, the correction unit may be capable of calculating a modified/corrected/calibrated sensor signal being less sensitive or even essentially independent of the viscosity of the sample. Therefore, the measurement accuracy may be significantly improved.

The correlation between the (change in) sensor signal and the viscosity may be assumed to follow theoretically derived equations, may be considered on the basis of empirical data and/or may be considered on the basis of an experimental relationship between the (change in) sensor signal and the viscosity obtainable by routine measurements of sensor signals and corresponding viscosity values. A corresponding correction curve or correction function may then be stored in the correction unit (as a mathematical function or as a look-up table) and may be used for performing the correction.

According to an exemplary embodiment of the invention, an integrated viscosity measurement of a sample may be performed for a high-resolution magnetic biosensor.

One of the benefits of a magnetic biosensor is the ability to perform measurements in a raw sample, because of the low interference of the sample with the magnetic detection principle. This may be especially an advantage for diagnostic or medical point-of-care applications, where the number of operator actions should be kept as small as possible.

Because of the intrinsically low reaction rates of immunoassays, it may be advantageous that measurements are carried out in the kinetic regime. Measurement in the kinetic regime may lead to lower detection limits or shorter measurement times. Depending on the application different trade-offs can be made between these two aspects. In the kinetic regime, the observed change of the sensor signal may be proportional to the concentration of the analyte and to the intrinsic reaction or transport rates of the involved processes. These latter may depend on the viscosity of the sample. So availability of the viscosity measurement may lead to either a more sensitive system or a system with short measurement time or both.

When measurements are performed in a raw sample, the properties of the sample cannot be fully controlled. As a consequence, the viscosity of the sample may vary to a certain degree. This may have consequences for the operation of the magnetic biosensor, since the viscosity may have an influence on the rate of change of the sensor signal. For example, it is believed that collecting the magnetic labels at the sensor surface scales directly with the viscosity. As a consequence less labels-surface interactions will take place and therefore the binding process will be slower at a higher viscosity. Even with the same concentration of magnetic labels near the surface, the binding process is expected to be slower in a sample with higher viscosity, because the Brownian movement of the labels is slowed down. This may also lead to a smaller rate of change of the sensor signal.

The rate of change of the sensor signal should only be a function of the concentration of target molecules, therefore the influence of the viscosity of the sample on the sensor reading may be reduced or minimized by exemplary embodiments of the invention.

According to an exemplary embodiment of the invention, it is possible to measure the viscosity of the sample in the magnetic biosensor and to correct the results for viscosity influences.

In particular, it is possible to measure the viscosity of the sample by magnetophoresis: a magnetic force may be applied to a magnetic label and the speed of the magnetic label may be measured. The force $F_m$ applied to a magnetic label can be expressed as:

$$F_m = \chi_{bead} \nabla \left( \frac{B^2}{2\mu_0} \right)$$

where $\chi_{bead}$ is the magnetic susceptibility of a magnetic label, B is the magnetic induction and $\mu_0$ is the permeability of free space. When a magnetic label moves with respect to the liquid, it experiences a drag force. This drag force can be approximated with Stokes' formula for drag on a spherical particle:

$$F = 6\pi\eta r v$$

where $\eta$ is the viscosity of the sample, r is the radius of the magnetic label and v is the velocity of the magnetic label. When the above formulas for magnetic force and drag force are combined, the following expression for the speed of a magnetic label is obtained:

$$v = \frac{\chi_{bead} \nabla \left( \frac{B^2}{2\mu_0} \right)}{6\pi\eta r}$$

From this formula, it can be seen that the velocity of a magnetic label scales directly with the viscosity of the liquid. The speed can be determined by moving the magnetic labels over a known distance and by measuring the time required to cover this distance. Since a magnetic sensor is already present in a magnetic biosensor, it may be favorable to use this magnetic sensor synergetically to perform such a measurement.

Above, mainly magnetic labels, magnetic forces and magnetic detection are discussed, but many combinations are possible of the force field (electric, magnetic, gravitational, centrifugal, etc.), the type of labels (magnetic, non-magnetic, conductive, non-conductive, etc.) and the detection technology (optical, acoustic, magnetic, electro-chemical etc.).

However, also other sensing principles can be used to detect the arrival of the magnetic labels near the surface.

The sensor can be any suitable sensor based on the detection of magnetic properties of particles on or near to a sensor surface, e.g. a coil, a wire, magneto-resistive sensor, magneto-strictive sensor, Hall sensor, planar Hall sensor, flux gate sensor, SQUID, magnetic resonance sensor, etc.

The device and method can be used with several biochemical assay types, e.g. binding/unbinding assay, sandwich assay, competition assay, displacement assay, enzymatic assay, etc.

In addition to molecular assays, also larger moieties can be detected, e.g. cells, viruses, or fractions of cells or viruses, tissue extract, etc.

The device, methods and systems according to embodiments of the invention are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device, methods and systems described herein can be used as rapid, robust, and easy to use point-of-care biosensors for small sample volumes. The reaction chamber can be a disposable item to be used with a compact reader. Also, the device, methods and systems according to embodiments of the present invention can be used in automated high-throughput testing. In this case, the reaction chamber is e.g. a well plate or cuvette, fitting into an automated instrument.

According to an exemplary embodiment of the invention, the magnetic particles can be stored on the top of a sample chamber before the measurement starts. The particles are then pulled down by magnetic forces towards the bottom of the sample chamber where the magnetic sensor element is located. The arrival of the magnetic labels at the bottom surface of the sample chamber is detected with the magnetic sensor. The time it takes for the magnetic labels to cover the distance from the top of the sample chamber to its bottom can be directly correlated with the viscosity of the sample. This viscosity measurement can be used to correct the sensor signal for viscosity effects, making the sensor robust against fluctuations in viscosity.

According to another exemplary embodiment of the invention, the magnetic labels may be pulled over the surface of the magnetic biosensor. One option is to release the labels from a known distance to the magnetic sensor element and pulling them towards/over this magnetic sensor element. The time needed to cover the distance to the sensor can be measured to calculate the viscosity of the liquid. The labels can be released by dissolution, addition of a fluid and/or by magnetic forces.

Another option is to move the magnetic labels over the surface of the sensor, where they pass at least two magnetic sensor elements. Dividing the distance between the two magnetic sensor elements by the time it takes the labels to cross the distance between the two sensor elements yields the speed of the magnetic labels. Again, the particle speed can be used to calculate the viscosity of the liquid, which in its turn can be used to compensate the sensor reading for viscosity effects.

According to another exemplary embodiment of the invention, the viscosity of the sample may be controlled (for instance by dilution, extraction, and/or filtration). In order to achieve the final accuracy level, the remaining viscosity variations may be corrected for by using one of the methods described in the previous embodiments.

It is also possible to directly measure the velocity of the magnetic labels than measuring the average speed of the labels over a known distance as described above.

Besides magnetic detection of the labels it is also possible to use other detection principles (for instance optical or electrical). However, since a magnetic sensor element is already available in a magnetic biosensor it may be advantageous to use magnetic detection to measure the speed of the magnetic labels.

It is also possible to measure the viscosity of a fluidic sample by bringing the particles into vibration by means of a varying magnetic field (such a principle is disclosed as such in US 2005/0155415 A1). Phase and/or amplitude information may be used to measure the viscosity of the liquid. In this case, the particle size does not need to be known as extra information is obtained from the measurement itself.

Magnetic biosensors are suitable to perform measurements in raw sample. However, the viscosity of an untreated sample cannot be fully controlled. The viscosity of the sample influences the sensor signal, which can lead to measurement errors. According to an exemplary embodiment of the invention, it is possible to measure the viscosity of the sample by magnetophoresis or any other magnetic measurement principle. A magnetic force is applied to the magnetic labels and their speed is measured. The speed can be directly related to the viscosity of the sample. The viscosity reading can be used to correct the measurement for viscosity influences. It may be attractive to use the magnetic sensor element of the magnetic biosensor to measure the speed of the magnetic labels.

In a bio-sensor, the influence of a variation of viscosity can therefore be suppressed by an integrated measurement of the viscosity through a measurement of time for the movement of magnetic particles over a known distance under the influence of an electro-magnetic field.

Next, further exemplary embodiments of the sensor device will be explained. However, these embodiments also apply to the method, to the program element and to the computer-readable medium.

The sensing unit may be adapted for sensing a detection signal indicative of the presence of magnetic particles. Accordingly, the viscosity measurement may be adapted for measuring the viscosity of the magnetic particles of the sample. The detection of magnetic particles may have the advantage that the detection signal and the viscosity measurement signal may be acquired on the basis of one and the same material, namely the magnetic particles such as magnetic beads. This measure may be based on the recognition that both the quantitative detection of the presence of the magnetic particles and the viscosity in the sample may be measured with the same probes, namely the magnetic particles. This may allow to easily incorporate a viscosity correction in a magnetic particle detection system.

The viscosity measurement unit may be adapted for measuring the viscosity of the sample by an actuation and by a detection. The actuation may comprise at least one of the group consisting of a magnetic actuation, an optical actuation, and an electrical actuation. The detection may comprise at least one of the group consisting of a magnetic detection, an optical detection, and an electrical detection. Magnetophoresis is an example for a magnetic actuation. Any one of a magnetic, optical, and electrical actuation may be combined with any one of a magnetic, optical, and electrical detection. For a magnetic biosensor, the combination of a magnetic actuation and a magnetic detection is a proper selection. Also the combination of a magnetic actuation and an optical detection is a proper selection. The viscosity measurement unit may be particularly adapted for measuring the viscosity of the sample by magnetophoresis. Magnetic measurements of the viscosity may include the measurement of vibrations of a time-dependent magnetic field. However, it is also possible to move magnetic particles under the influence of an applied external magnetic force and to measure a time needed for the particles to move along a surface having known geometry parameters. In the context of an optical measurement, optical properties of the sample depending on the viscosity may be used as a detection signal. An electrical measurement of the viscosity may, for instance, include the application of an electric field and the measurement of a time which electrically charged particles need to move along a defined distance in this electric field.

Particularly, the viscosity measurement unit may be adapted for measuring the viscosity of the sample by applying a magnetic force to the sample and by measuring a velocity of magnetic particles of the sample in response to the applied magnetic force. In this context, the viscosity measurement unit may be adapted for measuring the velocity of the magnetic particles by measuring a time required by the magnetic particles for moving along a predefined distance. It may be advantageous to use the same magnetic field source and same magnetic field detector for detecting both the viscosity of the sample and the detection signal indicative of the presence of the magnetic particles. Therefore, two independent and separately performed measurements may be carried out to accurately detect the quantity of the magnetic particles being present in a sample.

The sensor device may particularly comprise a pair of two magnetic field generators with overlapping reaches that can both selectively be activated by the viscosity measurement unit. In this context, the "reach" of a magnetic field generator is defined as the region in which the (typical) magnetic field generated by said field generator has observable effects on a (typical) magnetic particle, e.g. a magnetization or a particle movement. Magnetic particles in the region of overlapping reaches can therefore selectively be actuated by any one of the two magnetic field generators. It is thus for example possible to first collect all magnetic particles in a particular starting region by an activation of a first magnetic field generator, and then start their transition to the second magnetic field generator by activating this one and deactivating the first one. This allows to establish well-defined conditions for measuring the movement velocity of magnetic particles in a magnetic field, which comprises the desired information about the viscosity of the surrounding sample.

In a further development of the aforementioned embodiment, the sensor device comprises a magnetic sensor unit disposed adjacent to at least one of the two magnetic field generators for detecting the transition of magnetic particles between the two magnetic field generators. When the activation is switched from one magnetic field generator to the other and the corresponding transition movement of the magnetic particles starts, the magnetic sensor unit can determine the time that the particles need to accomplish this transition (or at least a characteristic stage of the transition). This can for example be achieved by detecting the arrival of magnetic particles at the newly activated field generator and/or by detecting the disappearance of magnetic particles from the previously activated magnetic field generator.

In the aforementioned embodiment, the magnetic sensor unit may for example be disposed between the two magnetic field generators; in this case, magnetic particles will cross the magnetic sensor unit during their transition from the first to the second magnetic field generator, which can readily be detected. According to another embodiment, the sensor device comprises two magnetic sensor units that are disposed at opposite sides of the pair of magnetic field generators. Thus differential measurements with an improved accuracy can be performed. Moreover, the field generators can be disposed very close to each other, which allows to generate high magnetic field gradients with comparatively little effort (currents). The transition of magnetic particles from one field generator to the other is detected in this scenario by the two magnetic sensor units disposed adjacent to the first and the second magnetic field generator, respectively.

Although the words upper, lower, right, left are used in the following description, the orientation of the (bio)sensor does not play an essential role. Thus, the terms upper and lower may be exchanged, and the terms left and right may be exchanged.

The viscosity measurement unit may be adapted for measuring the viscosity of the sample by applying a magnetic force to magnetic particles of the sample located in an upper portion of the sensor device and by vertically moving the magnetic particles of the sample in response to the applied magnetic force to measure a time interval until the magnetic particles reach a lower portion of the sensor device. According to such an embodiment, particles can be stored/accumulated on top of a sample chamber before a measurement starts. Pulling down the particles by magnetic forces (which may be generated by homogenous or inhomogeneous magnetic fields) towards the bottom of the sample chamber may allow to detect a time until arrival of the magnetic labels at the bottom surface. This can be taken as a basis for the viscosity measurement.

Alternatively, the viscosity measurement unit may be adapted for measuring the viscosity of the sample by applying a magnetic force to magnetic particles of the sample and by horizontally moving the magnetic particles of the sample in response to the applied magnetic force to measure a time interval until the magnetic particles reach a predefined destination of the sensor device. Particularly, in such an embodiment, the magnetic particles may be moved along a horizontal surface of a magnetic sensor device, for instance between two adjacent magnetic field sensors of a magnetic field sensor array. Releasing the labels from a known distance to the magnetic sensor elements and pulling them towards/over this magnetic sensor element may allow to measure viscosity and perform the detection of the magnetic particles. It is possible that the magnetic particles are moved over the surface of the sensor to pass at least two magnetic sensor elements.

According to another approach comprised by the invention, the viscosity measurement unit is adapted for measuring the viscosity of the sample by monitoring the formation and/or the breaking-up of chains of magnetic particles. In this context, the term "monitoring" shall comprise any procedure that is able to detect different stages of a process, for example via continuous measurements or via just two samplings at a starting-point and an end-point. The proposed measurement principle is based on the observation that magnetic particles tend to line up in chains or pillars under appropriate conditions (e.g. a sufficiently high magnetization and sufficiently low thermal or hydrodynamic disruption forces), and that the kinetics of the chain formation and chain breaking is related to the viscosity of the surrounding medium.

In a particular realization of the aforementioned approach, the sensor device comprises a magnet—called "chain-formation magnet" in the following—for selectively generating a "chain-forming" magnetic field inside the sample, wherein chains of magnetic particles can build-up in this chain-forming magnetic field. Such a design is particularly useful for magnetisable particles in which the chain-forming magnetic field first induces a magnetization and then makes the magnetized particles to line up in chains. With the chain-formation magnet, the regions in which the chains form, the orientation of the chains, and the timing of chain formation can readily be controlled to optimally fit to the detection capabilities of the viscosity measurement unit.

The chain-formation magnet is preferably adapted to selectively generate chain-forming magnetic fields inside the sample in at least two different (non-parallel) directions, for example parallel or perpendicular to a sensitive surface of the sensor device. It will then be possible to sequentially (i) form chains of a first direction, (ii) break-up these chains, and (iii) rearrange the magnetic particles in chains of a second direction. Such a transition between two different chain configurations may yield a stronger and clearer signal than for example the transition between chains and "normally" (i.e. randomly) distributed magnetic particles.

In another embodiment of the sensor device that applies the principle of chain formation, said device comprises a magnetic field generator for generating a "chain-disrupting magnetic field" inside the sample which breaks-up existing chains of magnetic particles. This embodiment can particularly be combined with the one that uses a chain-formation magnet for selectively building up chains of magnetic particles. Existing, stable chains of magnetic particles can then selectively and locally be disrupted by activating the magnetic field generator, wherein the speed of this disruption depends on the viscosity of the surrounding medium. After activation of the magnetic field generator, the magnetic particles from the affected chains will typically collect at the magnetic field generator where they can be detected by an associated sensor (e.g. a GMR sensor). The magnetic field generator can simultaneously serve as a component of such a magnetic sensor system that detects the presence of magnetic particles.

In a further development of the sensor device with chain formation measurement, the sensing unit has different sensitivities for the presence of magnetic particles in regions of chain formation and in regions where no chains of magnetic particles are formed. The same ensemble (number) of magnetic particles will then generate different detection signals in the sensing unit if arranged in chains or if normally distributed. The sensing unit can therefore be used for monitoring the formation and/or breaking-up of chains. In a typical case, the sensing unit will have a high sensitivity for magnetic particles close to a sensitive surface. This can be exploited by orienting the chains perpendicular (or parallel) to said surface, yielding a comparatively low (or high) detection signal for the chain-forming state.

The sensor device can optionally comprise an optical sensor system for optically detecting the formation and/or breaking-up of chains of magnetic particles. This optical sensor system may completely or partially be identical to the sensing unit, or it may be a system of its own. The optical sensor system may particularly detect the formation of chains by observing a change in light transmission, light reflectance, and/or in frustrated total internal reflectance. The latter method is highly sensitive in a small volume adjacent to a surface where (frustrated) total internal reflection of light occurs.

The sensor device may further comprise a viscosity adjustment unit adapted for adjusting the viscosity of the sample to obtain a predefined viscosity value. In response to a measured viscosity, the desired viscosity value may be adjusted by taking measures like dilution, extraction or filtration so as to adjust the viscosity to a defined value. Therefore, "standard" conditions can be generated which may make measurements highly reproducible and accurate.

The sensing unit may be adapted for sensing the detection signal in a portion of the sensor device differing from another portion of the sensor device in which the viscosity measurement unit is adapted for measuring the viscosity. Therefore, a first sensor portion of the sensor device may be provided for quantitatively detecting the (change of) the detection signal, and a second sensor portion may be provided for measuring the viscosity. Therefore, the two measurements may be decoupled so as to avoid undesired crosstalk between the two measurement events.

The device may be adapted for sensing the detection signal based on magnetic particles being bound at a sensing surface, and may be adapted for measuring the viscosity based on unbound magnetic particles. The actual quantitative particle detection may be based on the generation of hybridization events between immobilized capture molecules on the one hand and complementary particles to be detected and having magnetic beads attached thereto on the other hand. Such hybridization events may be used for the detection of the magnetic particles in a quantitative manner. Other beads or particles to be detected having attached beads may remain unbound at a sensor surface having capture molecules and may be used for being moved to perform viscosity measurements. Therefore, one and the same sample may be used for the quantitative estimation of the particle concentration and for the viscosity measurement of the sample for calibration purposes.

The sensor device may comprise a magnetic field generator adapted for generating a magnetic field for at least one of the group consisting of the detection of the presence of the particles, and the measurement of the viscosity of the sample. Such a magnetic field generator may be monolithically integrated in a substrate and may be a wire to which a current can be applied. Therefore, a magnetic field can be generated which may allow both the detection of the particles, for example using the Giant Magnetoresistance Effect, and the magnetically based measurement of the viscosity.

The correction unit may be adapted for correcting the detection signal under consideration of a correlation between the measured viscosity and a change in the detection signal with time. The change in the detection signal with time is a particularly sensitive measure for the quantity of the particles in the sample. On the other hand, the change in the detection signal with time does not only depend on the concentration of the particles but also on transfer rates which may be viscosity-dependent. Therefore, by using a pre-known, pre-calculated or pre-measured correlation function between the change in the detection signal and the viscosity, a correction can be performed which increases the accuracy of the measurement. Such information may be stored in the sensor device in a look-up table, as a mathematical function, etc.

The sensing unit may be adapted for quantitatively sensing the particles. In other words, not only the presence or absence of the particles may be detected, but also an amount of particles or a concentration of particles being present in the sample. This function may be further improved by the correction feature allowing to correct a determined quantity by eliminating artefacts resulting from viscosity changes.

The sensor device may be adapted for sensing the magnetic particles based on an effect of the group consisting of GMR, AMR, and TMR. Particularly, a magnetic field sensor device may make use of the Giant Magnetoresistance Effect (GMR) being a quantum mechanical effect observed in thin film structures composed of alternating (ferro)magnetic and non-magnetic metal layers. The effect manifests itself as a significant decrease in resistance from the zero-field state, when the magnetization of adjacent (ferro)magnetic layers are antiparallel due to a weak anti-ferromagnetic coupling between layers, to a lower level of resistance when the magnetization of the adjacent layers align due to an applied external field. The spin of the electrons of the nonmagnetic metal align parallel or antiparallel with an applied magnetic field in equal numbers, and therefore suffer less magnetic scattering when the magnetizations of the ferromagnetic layers are parallel. Examples for biosensors making use of the Giant Magnetoresistance Effect (GMR) are disclosed in WO 2005/010542 or WO 2005/010543.

The magnetic sensor device may be adapted for sensing magnetic beads attached to biological molecules. Such biological molecules may be proteins, DNA, genes, nucleic acids, polypeptides, hormones, antibodies, etc.

Therefore, the sensor device may be adapted as a magnetic biosensor device, that is to say as a biosensor device operating on a magnetic detection principle.

At least a part of the magnetic sensor device may be realized as a monolithically integrated circuit. Therefore, components of the magnetic sensor device may be monolithically integrated in a substrate, for instance a semiconductor substrate, particularly a silicon substrate. However, other semiconductor substrates are possible such as germanium, or any group III-group V semiconductor (like gallium arsenide or the like).

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

DESCRIPTION OF EMBODIMENTS

Figure 1:
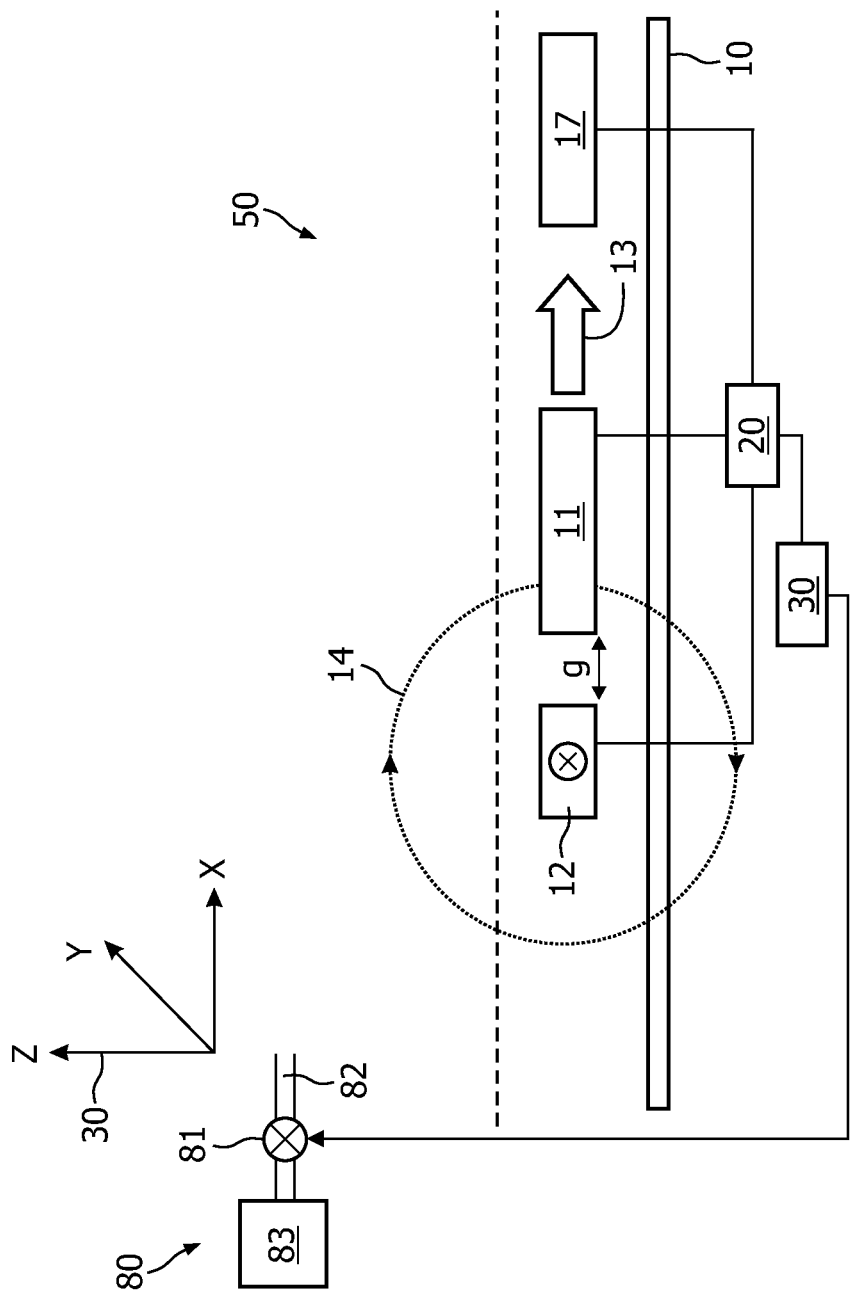
FIG. 1 illustrates a magnetic sensor device according to an exemplary embodiment in a first operation state.

The illustration in the drawing is schematically. In different drawings, similar or identical elements are provided with the same reference signs.

The device 50 according to an embodiment of the present invention is a biosensor and will be described with respect to FIG. 1 and FIG. 2.

The biosensor 50 detects magnetic particles 15 in a sample such as a fluid, a liquid, a gas, a visco-elastic medium, a gel or a tissue sample. The magnetic particles 15 can have small dimensions. With nano-particles are meant particles having at least one dimension ranging between 1 nm and 10000 nm, preferably between 10 nm and 3000 nm, more preferred between 100 nm and 1000 nm. The magnetic particles 15 can acquire a magnetic moment due to an applied magnetic field (for instance they can be paramagnetic). The magnetic particles 15 can be a composite, for instance consist of one or more small magnetic particles 15 inside or attached to a non-magnetic material. As long as the particles 15 generate a non-zero response to a modulated magnetic field, that is when their magnetic susceptibility deviates from the magnetic susceptibility of the surrounding medium, they can be used.

The device 50 may comprise a substrate 10 and a circuit, for instance an integrated circuit.

Figure 2:
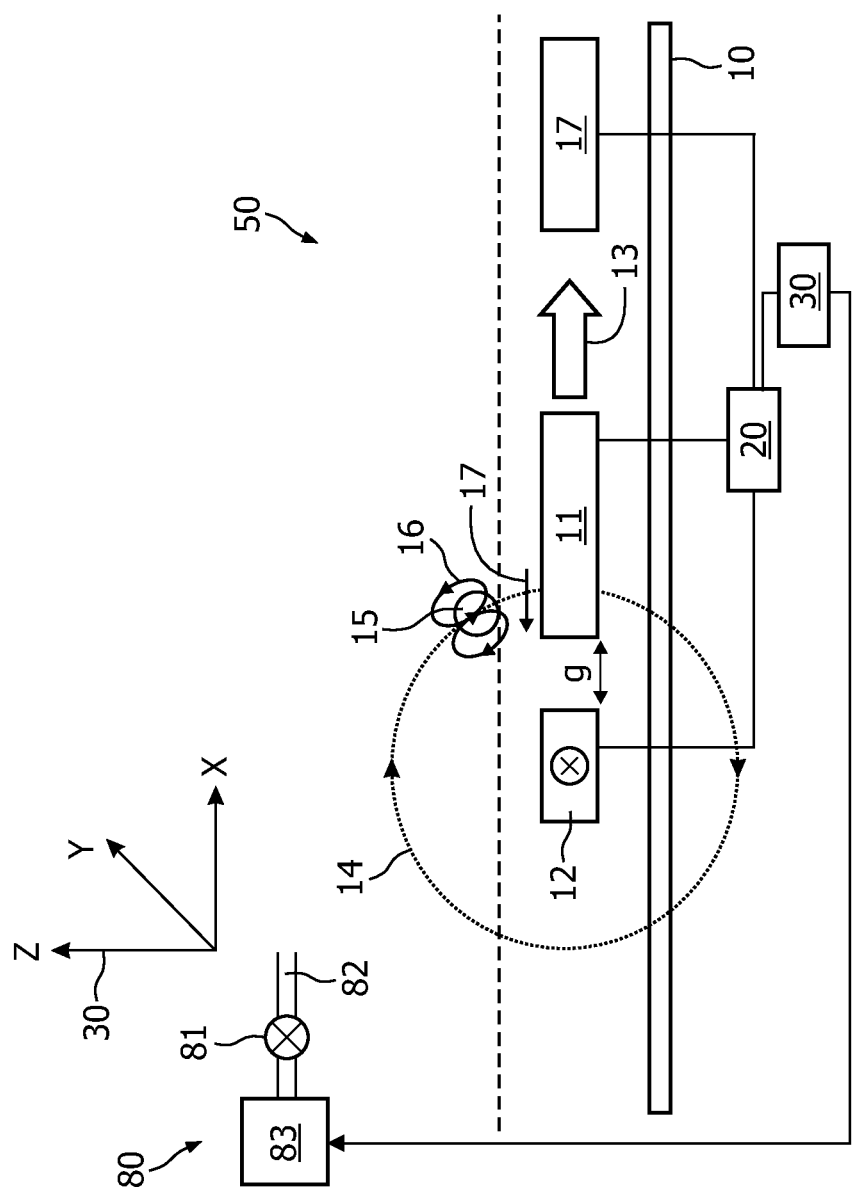
FIG. 2 illustrates the magnetic sensor device of FIG. 1 in a second operation state.

A measurement surface of the device is represented by the dotted line in FIG. 1 and FIG. 2. In embodiments of the present invention, the term "substrate" may include any underlying material or materials that may be used, or upon which a device, a circuit or an epitaxial layer may be formed. In other alternative embodiments, this "substrate" may include a semiconductor substrate such as for instance a doped silicon, a gallium arsenide (GaAs), a gallium arsenide phosphide (GaAsP), an indium phosphide (InP), a germanium (Ge), or a silicon germanium (SiGe) substrate. The "substrate" may include for example, an insulating layer such as a $SiO_2$ or an $Si_3N_4$ layer in addition to a semiconductor substrate portion. Thus, the term substrate also includes glass, plastic, ceramic, silicon-on-glass, silicon-on sapphire substrates. The term "substrate" is thus used to define generally the elements for layers that underlie a layer or portions of interest. Also, the "substrate" may be any other base on which a layer is formed, for example a glass or metal layer. In the following reference will be made to silicon processing as silicon semiconductors are commonly used, but the skilled person will appreciate that the present invention may be implemented based on other semiconductor material device(s) and that the skilled person can select suitable materials as equivalents of the dielectric and conductive materials described below.

The circuit may comprise a magneto-resistive sensor 11 as a sensor element and a magnetic field generator in the form of a conductor 12. The magneto-resistive sensor 11 may, for example, be a GMR or a TMR type sensor. The magneto-resistive sensor 11 may for example have an elongated, for instance a long and narrow stripe geometry but is not limited to this geometry. Sensor 11 and conductor 12 may be positioned adjacent to each other within a close distance g. The distance g between sensor 11 and conductor 12 may for example be between 1 nm and 1 mm; for instance 3 μm. The minimum distance is determined by the IC process.

In FIG. 1 and FIG. 2, a co-ordinate system is introduced to indicate that if the sensor device 50 is positioned in the xy plane, the sensor 11 mainly detects the x-component of a magnetic field, that is the x-direction is the sensitive direction of the sensor 11. The arrow 13 in FIG. 1 and FIG. 2 indicates the sensitive x-direction of the magneto-resistive sensor 11 according to an embodiment of the present invention. Because the sensor 11 is hardly sensitive in a direction perpendicular to the plane of the sensor device 50, in the drawing the vertical direction or z-direction, a magnetic field 14 caused by a current flowing through the conductor 12, is not detected by the sensor 11 in absence of magnetic nano-particles 15. By applying a current to the conductor 12 in the absence of magnetic nano-particles 15, the sensor 11 signal may be calibrated. This calibration may be performed prior to any measurement.

When a magnetic material (this can for instance be a magnetic ion, molecule, nano-particle 15, a solid material or a fluid with magnetic components) is in the neighborhood of the conductor 12, it develops a magnetic moment m indicated by the field lines 16 in FIG. 2.

The magnetic moment m then generates dipolar stray fields, which have in-plane magnetic field components 17 at the location of the sensor 11. Thus, the nano-particle 15 deflects the magnetic field 14 into the sensitive x-direction of the sensor 11 indicated by arrow 13 (FIG. 2). The x-component of the magnetic field Hx which is in the sensitive x-direction of the 12 sensor 11, is sensed by the sensor 11 and depends on the number of magnetic nano-particles 15 and the conductor current Ic.

For further details of the general structure of such sensors, reference is made to WO 2005/010542 and WO 2005/010543.

Reference numeral 20 in FIG. 1 and FIG. 2 illustrates a control unit coordinating the operation mode of the sensing unit 11 and of the magnetic field generator 12.

FIG. 1 and FIG. 2 show a sensor device 50 for sensing the particles 15 of a fluidic sample. As can be taken from FIG. 1 and FIG. 2, the sensor device 50 comprises a sensing unit 11, 20 adapted for sensing a detection signal indicative of the presence of the particles 15. The sensing unit 11, 20 has a measurement portion 11 at which the actual detection signal is generated, and has an evaluation or determining portion 20 (like a microprocessor or a CPU) in which the detection signal may be evaluated.

Additionally, a viscosity measurement unit 11, 17, 20 is provided which is adapted for measuring the viscosity of the sample. The viscosity of the sample is measured using the sensor surface 11 for generation of a signal used for determining the viscosity, the evaluation portion 20 and an additional active sensor surface 17 which is configured in a manner similar to the portion 11.

When the control unit 20 has calculated a viscosity value and a detection signal indicative of the presence of the particles 15, the calculation unit 30 forming a correction unit together with the unit 20 corrects the detection signal based on the measured viscosity.

Embodiments of the invention are based on the recognition of the inventors that different viscosity values of a sample may yield different magnetic detection signals, more particularly different changes in the magnetic detection signals in the presence of magnetic particles 15. Therefore, the unit 30 contains a look-up table reflecting a correlation of viscosity values and corresponding detection signals and corresponding concentrations so that, based on this correlation, the detection of the particles 15 may be corrected or calibrated for the present viscosity value in the sample.

The viscosity measurement unit 11, 17, 20 is adapted for measuring the viscosity of the sample based on magnetophoresis. More particularly, the viscosity measurement unit 11, 17, 20 measures the viscosity of the sample by applying a magnetic force by the magnetic field generation unit 12 to the sample and by measuring a velocity of the magnetic particles 15 in the sample in response to the applied magnetic force. The velocity of the particles 15 may be determined by measuring a time required by the magnetic particles 15 for moving along a predefined distance in a horizontal direction between sensor units 11 and 17. Therefore, the delay of the detection signal at the unit 17 compared to the unit 11 may allow to derive the viscosity value.

Furthermore, the sensor device 50 comprises a viscosity adjustment unit 80 controlled by the CPU 30 and adapted for adjusting the viscosity of the sample to obtain a predetermined viscosity value. When it is determined that the viscosity value is too large or too small, the unit 30 may control a valve 81 of the viscosity adjustment unit 80 so that through an inlet 82, fluidic material from a reservoir 83 may be supplied into the sample chamber to modify the viscosity, for instance by dilution with water or the like. This may allow to adjust a viscosity to a desired value when the unit 30 indicates the viscosity adjustment unit 80 that such a modification is desired.

The magnetic field generator 12 may generate a magnetic field for the detection of the presence of the particles 15 as well as for the measurement of the viscosity of the sample.

The correction unit 20, 30 corrects the detection signal under consideration of a correlation between the measured viscosity and a change in the detection signal with time. The gradient of the detection signal over time may be even more accurate for the quantity of the magnetic particles 15 and the detection signal itself. Therefore, such a derivative may be measured and may be corrected in accordance with the present viscosity value.

Figure 3:
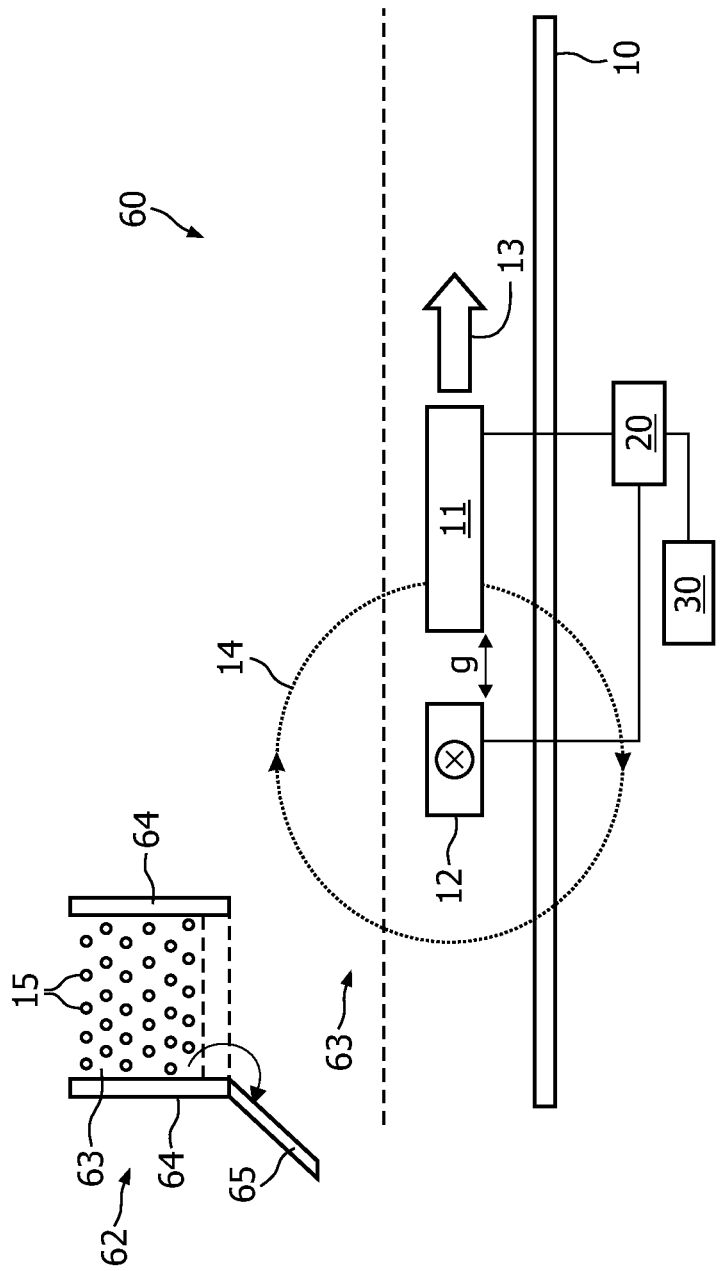
FIG. 3 to FIG. 7 illustrate magnetic sensor devices according to other exemplary embodiments of the invention.

FIG. 3 shows a sensor device 60 according to an exemplary embodiment of the invention.

In FIG. 3, the viscosity measurement unit 11, 20 is adapted for measuring the viscosity of the sample by applying a magnetic force to the magnetic particles 15 of the sample located in an upper portion 62 of the sensor device 60 and by vertically moving the magnetic particles 15 of the sample in response to the applied magnetic force to measure a time interval until the magnetic particles 15 reach a lower portion 63 of the sensor device 60.

More particularly, the magnetic particles 15 are stored in a storage chamber 63 having walls 64 and a pivotable bottom 65. Under the control of the units 20, 30, the bottom 65 may be opened to release the particles 15 out of the storage chamber 63. The particles 15 will then, under the influence of the magnetic field generated by the magnetic field generator 12 (and/or under the influence of gravity), move downwards to be detected after a certain time by the detector 11. This time may be measured. The start of a measurement may be triggered by an opening time of the bottom 65 (which may also be realized as a valve). The end of the time interval is defined by the point of time at which the detector 11 detects a magnetic signal.

Figure 4:
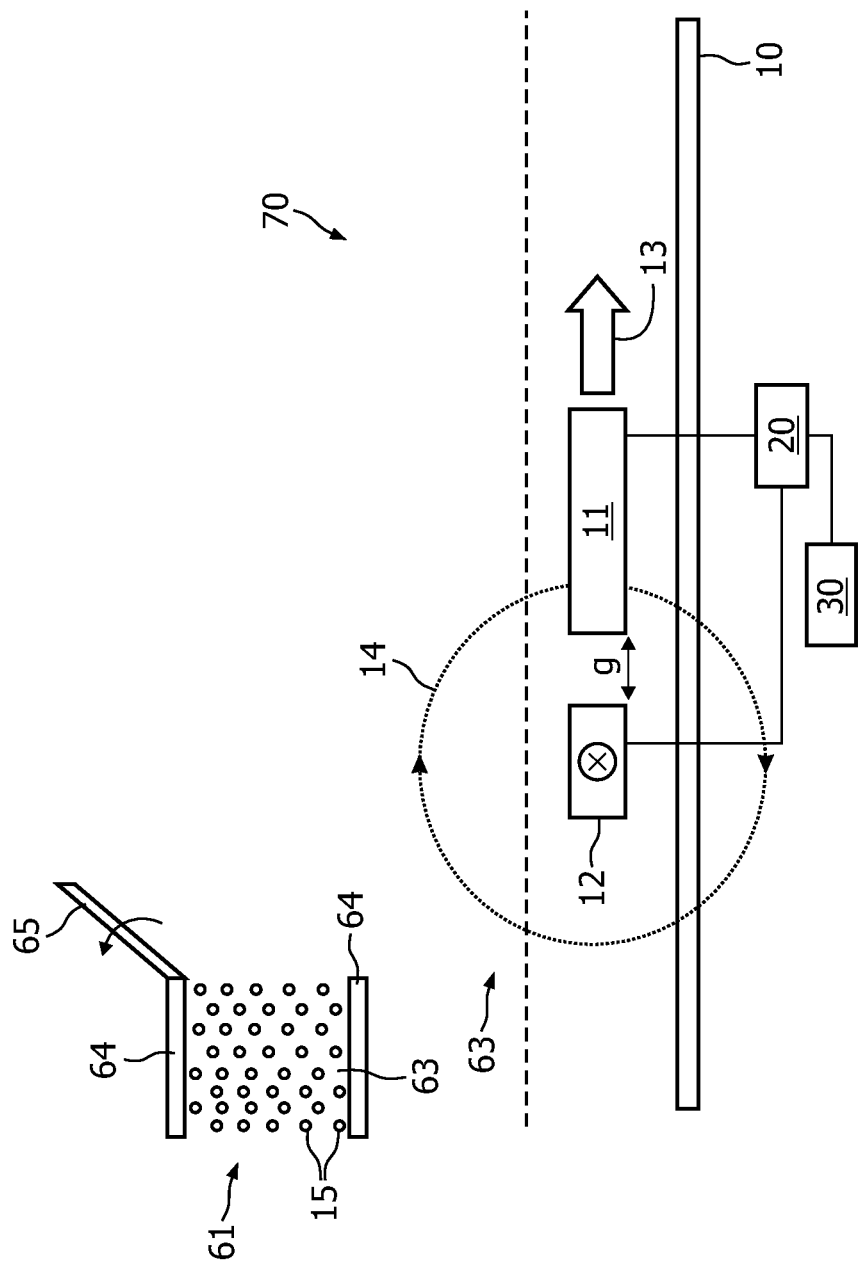

In a similar manner, as shown in FIG. 4, a sensor device 70 according to another exemplary embodiment of the invention has a viscosity measurement unit 11, adapted for measuring the viscosity of the sample by applying a magnetic force to the magnetic particles 15 of the sample and by horizontally moving the particles 15 of the sample in response to the applied magnetic force to measure a time interval until the magnetic particles 15 reach a predefined destination 11 of the sensor device 70. Therefore, after opening the bottom 65 by pivoting the latter, the particles 15 may be brought in a magnetic field generated by the magnetic field generator 12 and may be detected in a delayed manner by the detector 11. This time difference is an indication of the viscosity of the sample and allows the units 20, 30 to eliminate influences of viscosity when detecting a quantity of the particles 15.

Figure 5:
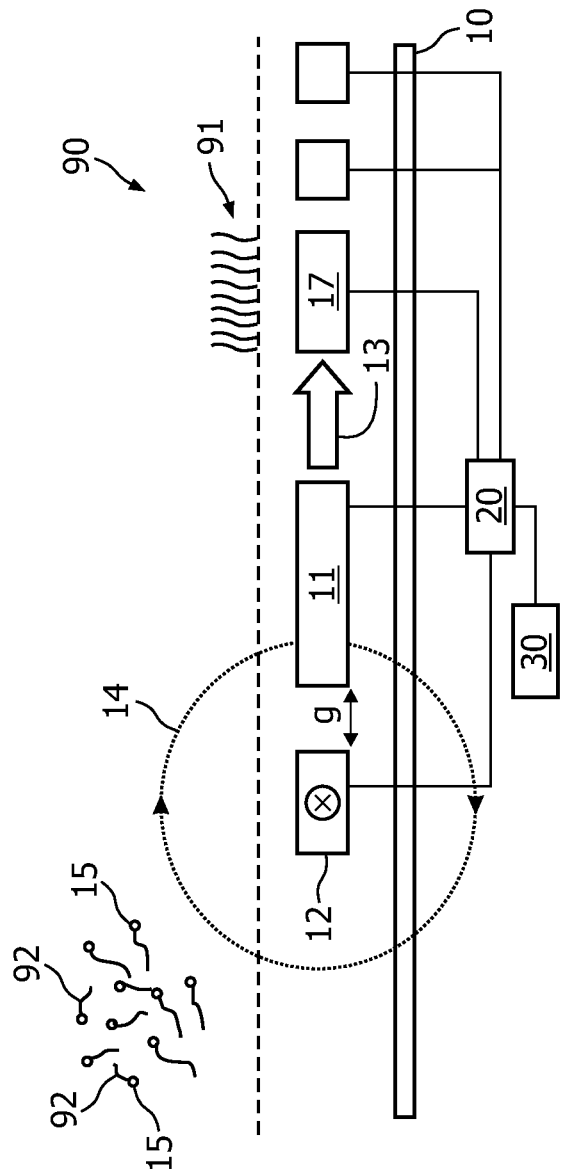

FIG. 5 shows a sensor device 90 according to another exemplary embodiment of the invention.

In FIG. 5, the molecules to be detected comprise biological molecules 92 having attached magnetic labels 15. The biological molecules 15 are adapted for selectively hybridizing with capture molecules 91 immobilized at a sensor surface close to the detector 17.

In accordance with FIG. 5, the sensing unit 17, 20 is adapted for sensing the detection signal in a portion of the sensor device 90 differing from another portion of the sensor device 90 in which the viscosity measurement unit 11, 17, 20 is adapted for measuring the viscosity. In other words, the detection unit 17 is adapted for measuring the presence of the particles 17, whereas a time difference of the arrival of the particles 15, 92 at the units 11 and 17 is taken as a basis for measuring the viscosity.

Therefore, the sensing unit 17, 20 is adapted for sensing the detection signal based on the magnetic particles 15 being bound at a sensing surface 91 and is adapted for measuring the viscosity based on unbound magnetic particles 15, 92.

It was already explained that the velocity v of a magnetic particle with susceptibility $\chi_b$ and hydrodynamic radius $r_h$ moving in a magnetic field gradient (magnetic induction B) can be expressed by $$v = \frac{1}{6\pi\eta r_h \lambda}\left(\chi_b \nabla\left(\frac{B^2}{2\mu_0}\right)\right),$$

wherein $\lambda$ is a correction factor for effects of a surface at distance $\delta$ from the particle. For distances $\delta/r<1$, the correction factor is $$\lambda = \frac{8}{15}\ln(\delta/r) + O(\delta/r)^0.$$

Because superparamagnetic particles are of nano- to micrometer scale, speed measurements are disturbed by the Brownian motion of the particles. To obtain a speed significantly larger than the Brownian motion, the following relation should apply over time (where D is the diffusion coefficient of the particles, including the thermal energy $k_B T$):

$$\int \frac{1}{6\pi\eta r_h} \chi_{bead} \nabla\left(\frac{B^2}{2\mu_0}\right) dt \gg 2\sqrt{\frac{Dt}{\pi}},$$

with $$D = \frac{k_B T}{6\pi\eta r_h}.$$

This relation shows that for nanometer-sized particles high field gradients are needed to obtain a sufficiently high speed. Typical values of $\nabla B^2$ for 300 nm particles are higher than 1

T$^2$/m. These high gradients can favorably be generated with integrated magnetic field generating wires on a chip.

Figure 6:
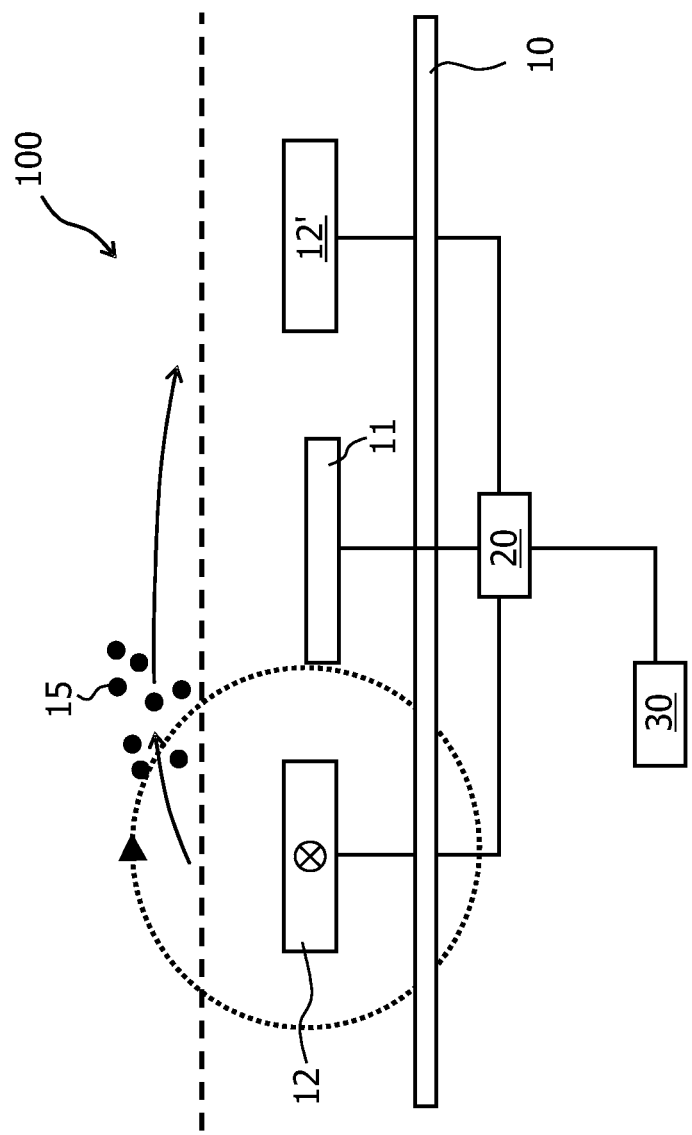

FIG. 6 shows one embodiment of a sensor device 100 with two such field generating wires 12, 12' that are disposed in a "wire-sensor-wire" configuration on both sides of a GMR sensor 11. In such a GMR biosensor 100, magnetic particles 15 can be applied to the chip surface in a dry-reagent layer. After wetting, the particles 15 are easily captured by an active wire, e.g. the left field generating wire 12. By deactivating this wire 12 and activating the other field generating wire 12', the particles 15 can be pulled over the GMR sensor 11 and the crossing-time can be measured.

Because the GMR sensor 11 is in between the wires 12, 12' in the arrangement of FIG. 6, there is a minimum distance between the wires 12, 12' of about 9 μm. The accuracy of viscosity measurements can be improved if the wires are closer together and the influence of Brownian motion is diminished.

Figure 7:
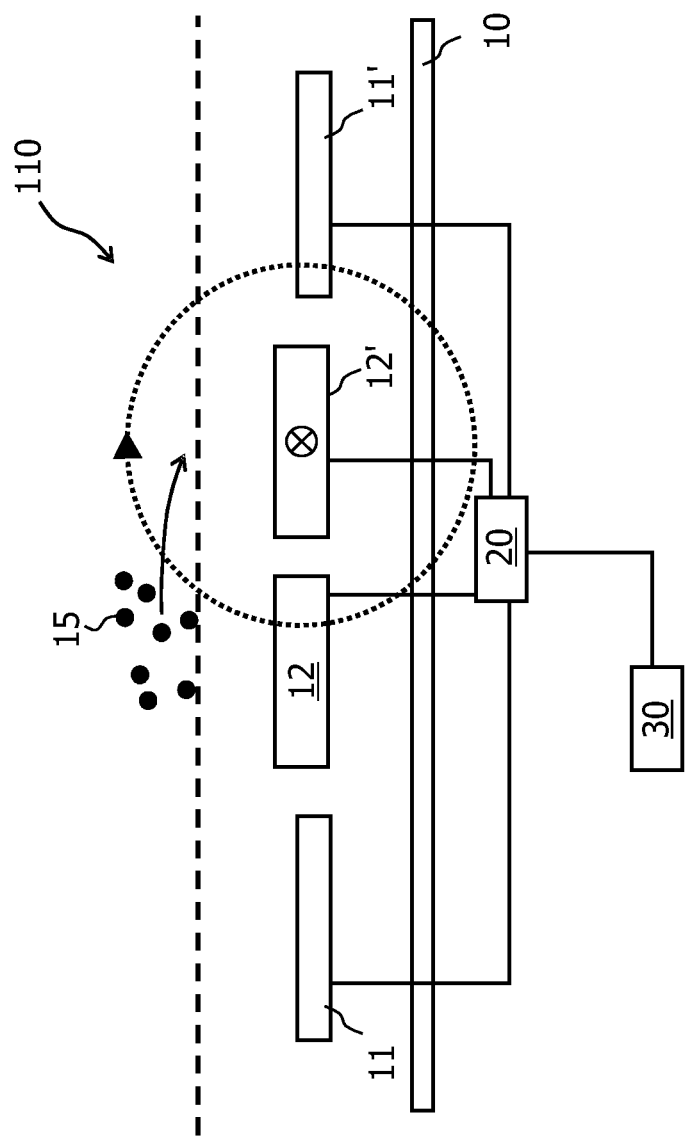

FIG. 7 therefore shows an alternative sensor device 110 with a "sensor-wire-wire-sensor" configuration in which the field generating wires 12, 12' can be closer together (up to about 1 μm). Two GMR sensors 11, 11' are disposed on both sides of the pair of wires 12, 12'. The first GMR sensor 11 is essential for measuring the crossing time, and the second GMR sensor 11' is beneficial because then a differential signal can be measured. The decrease in signal of one sensor can be compared to the increase of signal in the other sensor, and corrections can easily be made for outside disturbances. Thus a differential measurement with a higher accuracy can be performed.

Figure 8:
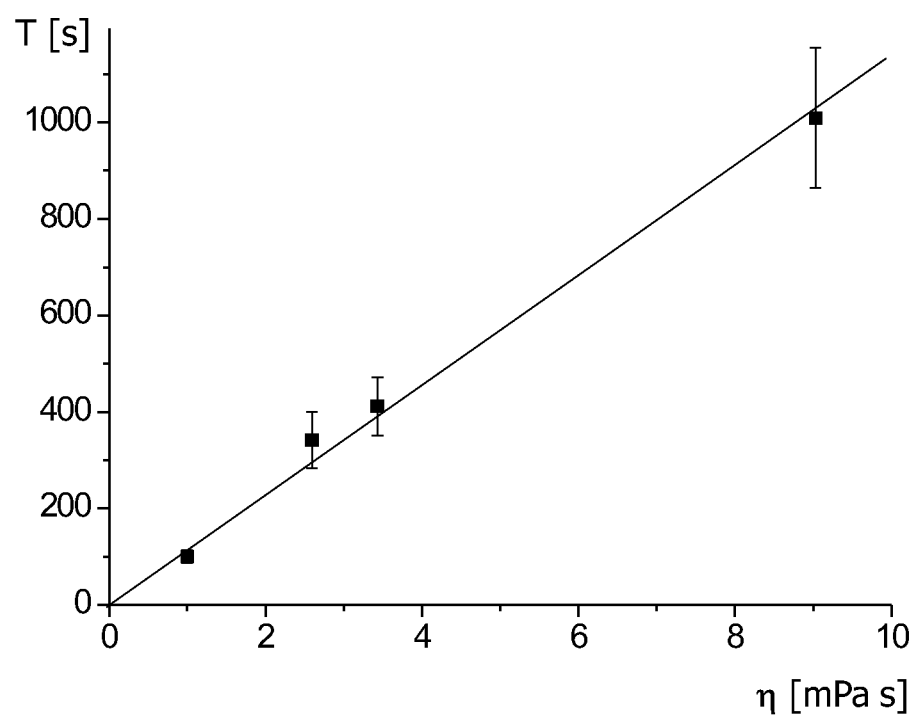
FIG. 8 shows in a diagram the correlation between sample viscosity and average crossing times in a setup like that of FIG. 6 or 7.

FIG. 8 shows in a diagram the average crossing time T (vertical axis) of magnetic particles in a setup like that of FIG. 6 or 7 versus the viscosity of the sample (horizontal axis). The experiments were performed with two magnetic field generating wires with a width of 3 μm separated by 3 μm. Sample solutions were made with different viscosities by adding glycerol. For each measured point approximately four different particles, each with 10 crossovers were used. The diagram shows that the crossing time depends inversely on the viscosity.

Measuring the viscosity is therefore possible on a GMR biosensor chip by using two current wires and one or two GMR sensors that measure the crossing time between the wires, which depends inversely on the viscosity of the fluid.

When the magnetic particles are moved orthogonal to the sensor surface of the sensor devices explained above, the distance that has to be covered is relatively large. This leads to a relatively low measurement frequency, which may be a problem in situations where the viscosity changes over time relatively quickly (e.g. due to blood coagulation). Moreover, moving the particles parallel over the surface to measure viscosity may be subject to particle-surface interactions (e.g. stickiness or roughness), which could deteriorate the accuracy of the measurement.

FIGS. 9 to 13 illustrate an alternative viscosity measurement principle that is suited to address the aforementioned issues. This principle or method makes use of the formation of chains 18 or pillars of magnetic particles 15 under influence of an applied magnetic field and of breaking them up again after removal of the applied magnetic field. Both the speeds of building and breaking-up of the chains/pillars can be used to measure the viscosity of the fluid. This will now be explained in more detail:

Superparamagnetic particles 15 (beads) in a magnetic field become magnetic and are able to attract other magnetic particles towards one of their pole surfaces. An ensemble of particles will therefore form chains 18 when exposed to an external magnetic field that are aligned with the magnetic field lines (provided that the field strength is high enough, so that the magnetic energy is larger than the thermal kinetic energy of the particles). In absence of a magnetic field or in a low magnetic field strength (magnetic energy<kinetic energy), the formed chains are instable and they break-up due to the Brownian motion of the particles.

A passive break-down of the chains happens spontaneously and cannot be controlled or accelerated. Besides this passive process, the breaking-up can be enforced in an active way, which means that the breaking-up is controllable to a certain extent. Active manners are for example the appliance of a magnetic force, electrical force, mechanical force, etc.

Figure 9:
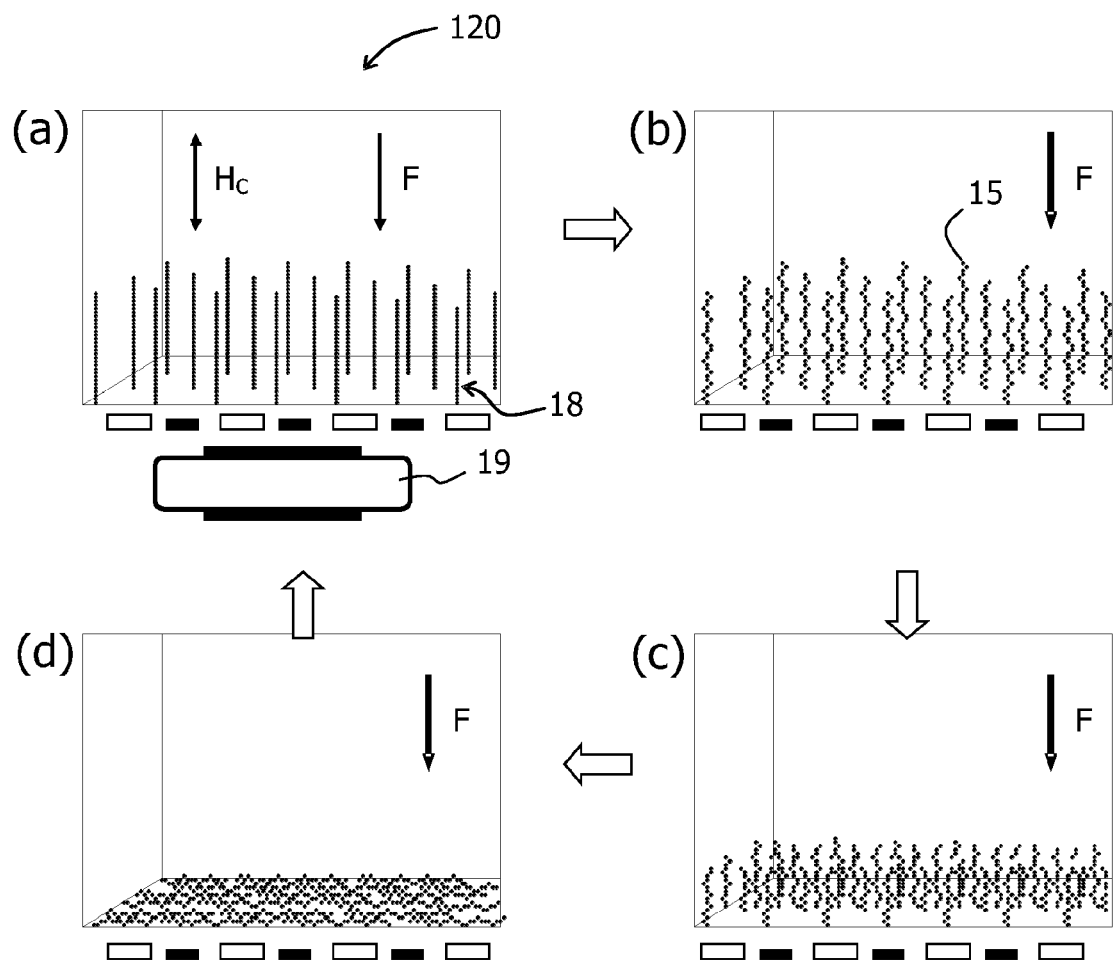
FIG. 9 to FIG. 13 show different scenarios of chain formation used for the determination of sample viscosity.

FIG. 9 shows as an exemplary measurement procedure in a sensor device 120 a repetition of building and breaking-up chains 18 of magnetic particles 15 in order to determine the viscosity of the fluid. The procedure starts in stage (a) with the formation of chains or pillars 18 by application of a "chain-forming magnetic field" $H_c$ generated with a "chain-formation magnet" 19. After switching this magnetic field off, the pillars 18 gradually decay under the influence of thermal forces (stage (b)) and gravitational forces F (stage (c)) acting on the particles 15 until the particles finally reach a stable distribution (stage (d)). The duration of this decay process to go from (b) to (d) depends on the viscosity. It can be measured with setups as shown in FIGS. 1 to 7 that detect the presence of magnetic particles at a sensitive surface.

Figure 10:
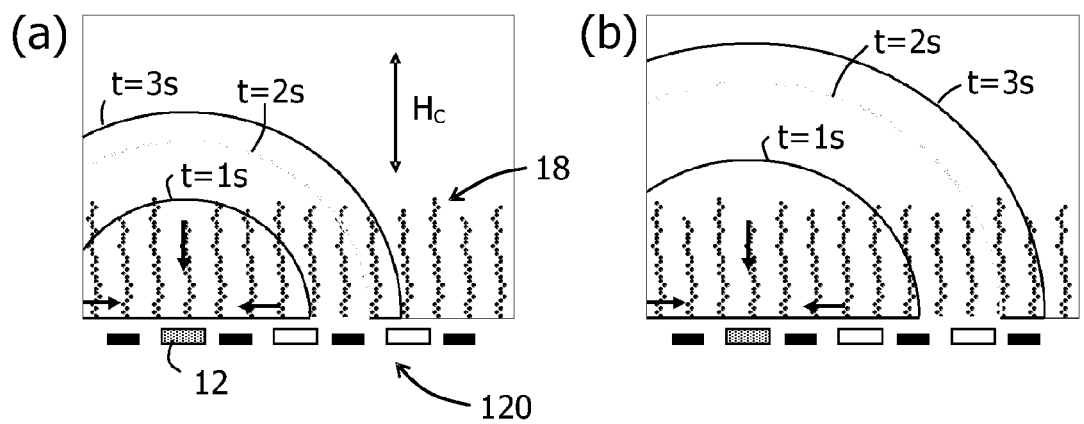

FIG. 10 illustrates an example of breaking-up chains 18 of magnetic particles in an active way. The chains 18 are generated and stabilized by a chain-forming magnetic field $H_c$. Integrated current wires 12 can then selectively generate a circular "chain-disrupting magnetic field", which is producing a superimposed magnetic force toward the wires. The speed at which the particles are then collected at the wires is a function of viscosity. For a higher viscosity it takes more time to collect the particles than in case of a lower viscosity. This is illustrated by three exemplary half-circles which encompass all particles that collect at the wires after t=1 s, t=2 s, and t=3 s, respectively. The radius of these lines—and therefore the collection speed—is a function of viscosity, which is higher in the left drawing (a) than in the right drawing (b).

Figure 11:
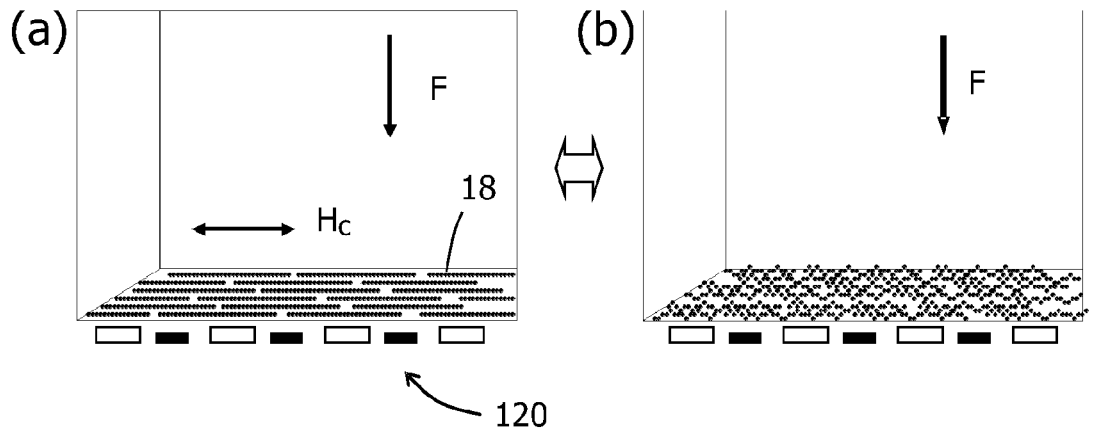

FIG. 11 shows an embodiment in which chains 18 of particles are formed in stage (a) parallel to the sensor surface due to a correspondingly oriented chain-forming magnetic field $H_c$. After removal of this magnetic field, the particles 15 start to move due to thermal motion (passive) in the plane of the surface but to a certain extent also away from the surface (stage (b)). The speed of the thermal motion depends on the viscosity and therefore the signal rate measured by the sensor device 120 depends on the viscosity, too. This phenomenon can quantitatively be observed with a detection system that measures only the particles that are in close contact with the surface, for example a detection system that applies frustrated total internal reflection (FTIR) of a light beam at the sensor surface with an evanescent wave entering a small volume of the sample space.

Figure 12:
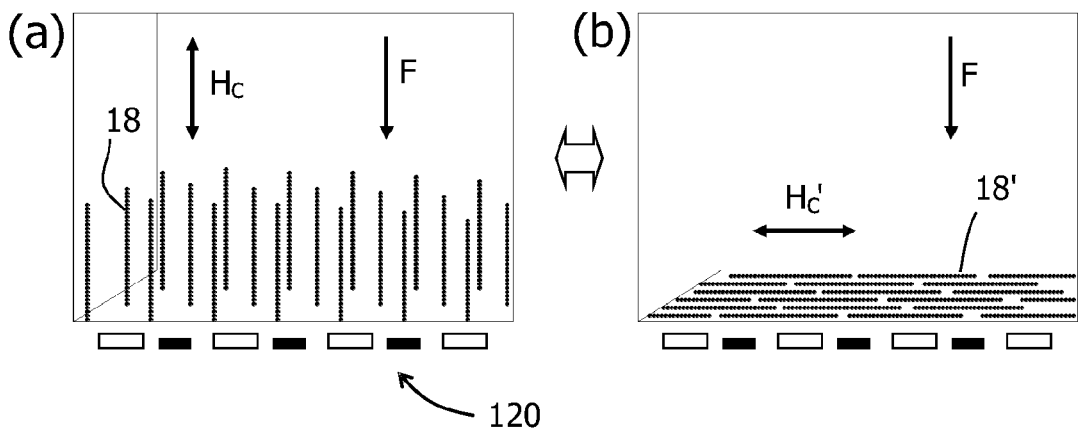

In the scenario of FIG. 12, chains 18 (or pillars) that are perpendicular to the sensor surface in stage (a) are actively transformed into chains 18' that are parallel to the sensor surface by switching between two correspondingly oriented magnetic fields $H_c$ and $H_c'$. The speed of changing from one state to the other is again dependant on the viscosity.

Figure 13:
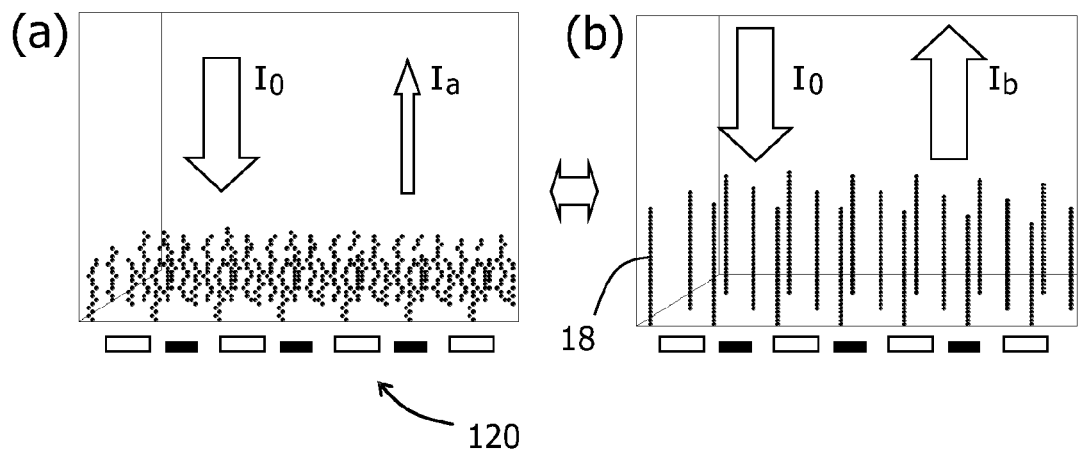

When the magnetic particles are formed into chains 18 (or pillars) perpendicular to a sensor surface, the breakdown of these chains 18 can be observed by optical observation from the top, as illustrated in FIG. 13. Preferably the chains are formed in this case on top of a reflective surface, such as e.g. a chip surface. When the particles 15 arranged in chains 18 (stage (b)), a substantial fraction $I_b$ of the incident light $I_0$ is reflected from this surface, since the chains tend to repel one another. When the particles break-away from the chains (stage (a)), the particles will block more of the reflected light, yielding a lower amount $I_a$ of reflected light. The speed at which the reflected light decreases is a measure of the viscosity of the liquid.

Instead of measuring reflection, it is also possible to use a transparent substrate and to detect the transmission of the incident light $I_0$.

In another embodiment, all the magnetic particles from a solution are pulled toward a binding surface using a magnetic field, such that they are located in chains, perpendicular to the sensor surface. When the magnetic field is switched off, the rate at which the particles bind to the surface is also a measure of viscosity.

It should be noted that the term "comprising" does not exclude other elements or features and the "a" or "an" does not exclude a plurality. Also elements described in association with different embodiments may be combined.

It should also be noted that reference signs in the claims shall not be construed as limiting the scope of the claims.

The invention claimed is:

1. A sensor device for sensing magnetic particles of a fluidic sample, the sensor device comprising:
    a sensing unit configured to sense a detection signal indicative of presence of the magnetic particles;
    a viscosity measurement unit configured to measure viscosity of the sample; and
    a correction unit for correcting the detection signal based on the measured viscosity, from a predetermined correlation between viscosity and change of the detection signal;
    wherein sensing unit comprises a sensing surface, the magnetic particles of the fluidic sample comprise unbound magnetic particles and bound magnetic particles bound to the sensing surface, the viscosity measurement unit is configured to measure the viscosity of the sample using the unbound magnetic particles and the sensing unit is configured to sense the detection signal indicative of the presence of the bound magnetic particles at the sensing surface.

2. The sensor device of claim 1, further comprising upper and lower portions, wherein the viscosity of the sample is measured by applying a magnetic force to the magnetic particles of the sample located in the upper portion and by vertically moving the magnetic particles of the sample under the influence of the applied magnetic force to measure a time interval until the magnetic particles reach the lower portion.

3. The sensor device of claim 1, wherein the viscosity measurement unit is configured to measure the viscosity of the sample by applying a magnetic force to the magnetic particles of the sample and by horizontally moving the magnetic particles of the sample under the influence of the applied magnetic force to measure a time interval until the magnetic particles reach a predefined destination.

4. The sensor device of claim 1, further comprising a viscosity adjustment unit for adjusting the viscosity of the sample to a predefined viscosity value.

5. The sensor device of claim 1, wherein the viscosity measurement unit is configured to measure the viscosity of the sample by actuation and detection.

6. The sensor device of claim 5, wherein the actuation is selected from at least one of a magnetic actuation, an optical actuation, and an electrical actuation.

7. The sensor device of claim 5, wherein the detection is selected from at one of a magnetic detection, an optical detection and an electrical detection 8. The sensor device of claim 1, wherein the magnetic particles of the fluidic sample comprise unbound magnetic particles and bound magnetic particles and the viscosity of the sample is measured by applying a magnetic field to the sample and by measuring a velocity of the unbound magnetic particles of the sample in response to the applied magnetic field.

9. The sensor device of claim 8, wherein the velocity of the unbound magnetic particles indicates a time required by the unbound magnetic particles for moving along a predefined distance in the applied magnetic field.

10. The sensor device of claim 8, further comprising a pair of magnetic field generators having overlapping reaches that are selectively activated by the viscosity measurement unit.

11. The sensor device of claim 10, further comprising a magnetic sensor disposed adjacent to at least one of the magnetic field generators for detecting transition of the unbound magnetic particles from one magnetic field generator to the other.

12. The sensor device of claim 10, further comprising two magnetic sensors disposed at opposite sides of the pair of magnetic field generators.

13. The sensor device of claim 1, wherein the magnetic particles of the fluidic sample comprise unbound magnetic particles and bound magnetic particles and the viscosity of the sample is measured by monitoring at least one of formation and breaking-up of chains of the unbound magnetic particles.

14. The sensor device of claim 13, further comprising a magnetic field generator for generating a chain-disrupting magnetic field inside the sample for breaking up the chains of the unbound magnetic particles.

15. The sensor device of claim 13, wherein the sensing unit has a different sensitivity for the presence of the magnetic particles in regions of chain formation than elsewhere.

16. The sensor device of claim 13, wherein the optical sensor is configured to detect the formation of chains of the magnetic particles via at least one of a change in transmission, reflectance and frustrated total internal reflectance.

17. The sensor device of claim 13, further comprising a chain-formation magnet for selectively generating a chain-forming magnetic field inside the sample in which chains of the unbound magnetic particles can build up.

18. The sensor device of claim 17, wherein the chain-formation magnet is adapted to selectively generate chain-forming magnetic fields in at least two different directions.

* * * * *